United States Patent [19]

Ishimaru

[11] Patent Number: 5,574,276

[45] Date of Patent: Nov. 12, 1996

[54] APPARATUS AND METHOD FOR DETECTING A DUST PARTICLE HAVING HIGH PURITY INERT GAS ATMOSPHERE

[75] Inventor: Toshiyuki Ishimaru, Kanagawa, Japan

[73] Assignee: Sony Corporation, Tokyo, Japan

[21] Appl. No.: 412,927

[22] Filed: Mar. 29, 1995

[30] Foreign Application Priority Data

Mar. 30, 1994  [JP]  Japan ................................ 6-083883

[51] Int. Cl.$^6$ .................................................. G01V 9/04
[52] U.S. Cl. .................................. 250/222.2; 250/559.4; 356/237
[58] Field of Search ................................. 250/574, 576, 250/559.11, 559.13, 559.22, 559.34, 559.4, 559.41, 222.2; 356/237, 338; 372/9, 22, 23, 24, 28

[56] References Cited

U.S. PATENT DOCUMENTS

| | | | |
|---|---|---|---|
| 5,214,486 | 5/1993 | DeWitt | 356/237 |
| 5,317,380 | 5/1994 | Allemand | 356/338 |
| 5,416,594 | 5/1995 | Gross et al. | 356/237 |

Primary Examiner—Que T. Le
Attorney, Agent, or Firm—Hill, Steadman & Simpson

[57] ABSTRACT

There is provided a dust particle inspection apparatus which comprises a laser beam source for emitting a laser beam having a coherence distance longer than 1 km; a scanner for scanning the surface of an article, which is to be inspected, with the emitted laser beam; an optical detector for detecting the laser beam reflected and diffracted on the surface of the article being inspected; a stage for setting the article thereon and displacing the same in a predetermined direction; and a gas supply means for surrounding the article with a high-purity inert gas atmosphere. There is also provided a dust particle inspection method which comprises the steps of surrounding the article under inspection with a high-impurity inert gas atmosphere; while displacing the article in a predetermined direction, scanning the surface of the article with a laser beam having a wavelength $\lambda$ and a coherence distance longer than 1 km; and detecting the laser beam reflected and diffracted on the surface of the article to thereby detect any dust particle or the like with high precision and certainty on the surface of the article such as a reticle.

9 Claims, 11 Drawing Sheets

APPARATUS AND METHOD FOR DETECTING A DUST PARTICLE HAVING HIGH PURITY INERT GAS ATMOSPHERE

BACKGROUND OF THE INVENTION

1. Field of the Invention

The present invention relates to a method and an apparatus for inspecting a dust particle and, more particularly, to a method and an apparatus adapted for inspection of a dust particle on a reticle or the like.

2. Description of the Related Art

In a semiconductor exposer, a reticle dust inspection apparatus is employed to detect a dust particle 5 deposited on the surface of a reticle 1. Such a reticle dust inspection apparatus is used normally in combination with a reticle changer. When the reticle 1 is displaced from a reticle cassette housing carrier in the reticle changer to a predetermined position in the semiconductor exposer or is returned therefrom, the reticle 1 is inspected by the reticle dust inspection apparatus.

An exemplary conventional reticle dust inspection apparatus known heretofore comprises a He-Ne or Ar laser beam source, a scanner for scanning the surface of an inspected article with a light beam emitted from the laser beam source, an optical detector for detecting the light beam reflected and diffracted on the surface of the inspected article, and a stage for setting the inspected article thereon and displacing the inspected article in a predetermined direction. Meanwhile the scanner consists of a polygon mirror and an f-θ lens for example, and the optical detector consists of a condenser lens and a photo sensor.

In inspection of a dust particle 5 on the surface of the reticle 1, first the reticle 1 is set on the stage. Then the stage is displaced by a driving mechanism in a predetermined direction (e.g., Y-direction), and simultaneously therewith the surface of the reticle 1 is irradiated, at an oblique incidence angle, with the light beam emitted from the He-Ne or Ar laser beam source, whereby the reticle surface is scanned at a certain angle formed with respect to the Y-direction. As typically illustrated in FIG. 1A, the laser beam is reflected from the surface of the reticle 1 in case none of dust particle is existent on the reticle surface. However, when a dust particle 5 or the like is existent on the reticle surface as typically illustrated in FIG. 1B, the laser beam is diffracted with diffused reflection by such dust particle 5. In this case, a portion of the diffracted beam 4 is selectively received by the optical detector and then is converted into an electric signal to detect the dust particle.

Diffraction of the laser beam 2 is caused also by a pattern formed on the reticle 1. The diffracted beam 4 resulting from the dust particle is projected omnidirectionally at predetermined diffraction angles. Meanwhile the diffracted beam 4 resulting from the pattern has such attribute that it is projected in a direction of 90° with respect to the pattern. The directions of the pattern formed on the reticle are generally at angles of 0°, 45° and 90° with the Y-direction. As illustrated in a typical plan view of FIG. 1C, the pattern and the dust particle 5 are strictly discriminated from each other by first irradiating the laser beam 2 to the reticle 1 in such a manner that the direction of the irradiated laser beam 2 to the reticle has a fixed angle α of, e.g. 75°, with the Y-direction, and then receiving merely the diffracted beam 4 at such angle α by the optical detector.

In the conventional reticle dust inspection apparatus, it is generally customary to employ a He-Ne or Ar laser beam source. Since such laser beam source has a low coherence with its coherence distance being approximately 0.1 m, so that the light intensity of the diffracted beam is low and the signal-to-noise ratio is inferior. Consequently there arises a problem that a high precision is not achievable in detection of a dust particle or the like. The minimum detectable size thereof is 0.7 μm or so. The light intensity of the diffracted beam can be increased by the use of a laser beam source having a longer coherence distance and a higher coherence, and therefore it is possible to enhance the precision in detecting a dust particle or the like. However, in the use of a laser beam source of a high coherence, another problem arises that a speckle pattern is generated due to corpuscles of ultrafine dust or the like floating in the air in an optical path proximate to the reticle, hence failing in proper detection of the dust particle existent on the reticle surface.

OBJECT AND SUMMARY OF THE INVENTION

It is therefore an object of the present invention to provide a dust particle inspection apparatus and method capable of exactly detecting the presence of a dust particle with high precision on the surface of an inspected article such as a reticle.

The above object can be achieved by the dust particle inspection apparatus of the present invention which comprises: (a) a laser beam source for emitting a laser beam having a certain coherence distance; (b) a scanner for scanning the surface of an article, which is to be inspected, with the laser beam emitted from the laser beam source; (c) an optical detector for detecting the light beam reflected and diffracted on the surface of the article; (d) a stage for setting the article thereon and displacing the same in a predetermined direction; and (e) gas supply means for surrounding the article with a high-purity inert gas atmosphere.

The spectral half-amplitude level $\Delta v$ of the laser beam emitted from the laser beam source and the coherence distance Lc thereof are approximately in a relationship of $\Delta v \times Lc \approx 1$. Although any inert gas may be used for the above high-purity inert gas atmosphere, it is preferred to use, for example, a nitrogen gas having a purity higher than 99%.

In the dust particle inspection apparatus of the present invention, it is preferred that the laser beam source comprises: (A) an LD-excited solid-state laser capable of emitting second harmonics and consisting of a laser diode, a solid-state laser medium composed of Nd:YAG, and a nonlinear optical crystal element; (B) a second harmonics generator consisting of a nonlinear optical crystal element and an optical resonator; and (C) a resonator length controller for controlling the resonator length of the optical resonator; wherein the light beam emitted from the LD-excited solid-state laser is caused to be incident upon the second harmonics generator, and a light beam having the wavelength based on the second harmonics of the incident light beam is emitted from the second harmonics generator. The laser beam source may be equipped with an optical path split means for partially causing the laser beam, which is emitted from the LD-excited solid-state laser, to be incident upon the scanner. Further a coherence distance reduction means may be disposed between the optical path split means and the scanner. It is also possible to dispose both an optical path split means for partially splitting the laser beam emitted from the second harmonics generator, and a coherence distance reduction means between the optical path split means and the scanner.

The object mentioned above can also be achieved by the dust particle inspection method of the present invention which comprises the steps of: surrounding an article, which is to be inspected, with a high-impurity inert gas atmosphere; then, while displacing the article in a predetermined direction, scanning the surface of the article with a laser beam having a wavelength A and a coherence distance longer than 1 km; and detecting the laser beam reflected and diffracted on the surface of the article to thereby detect any dust particle or the like on the surface of the article. In a preferred aspect of the dust particle inspection method according to the present invention, there may be further included a step of scanning the region of the inspected article, where any abnormal light intensity of the reflected and diffracted laser beam has been found on the surface of the article as a result of the foregoing scanning with the laser beam having a wavelength $\lambda$ and a coherence distance longer than 1 km, with another laser beam having a wavelength $\lambda'$ and a coherence distance longer than 1 km. In this case, it is preferred that the two laser beams having the wavelengths $\lambda$ and $\lambda'$ respectively are emitted from the same laser beam source, and this laser beam source comprises (A) an LD-excited solid-state laser capable of emitting second harmonics and consisting of a laser diode, a solid-state laser medium composed of Nd:YAG, and a nonlinear optical crystal element; (B) a second harmonics generator consisting of a nonlinear optical crystal element and an optical resonator; (C) a resonator length controller for controlling the resonance length of the optical resonator; and (D) an optical path split means for partially causing the laser beam, which is emitted from the LD-excited solid-state laser, to be incident upon the scanner; wherein the laser beam of the wavelength $\lambda$ or $\lambda'$ emitted from the LD-excited solid-state laser is caused to be incident upon the second harmonics generator, and the laser beam of the wavelength $\lambda'$ or $\lambda$ based on the second harmonics of the incident beam is emitted from the second harmonics generator.

In another preferred aspect of the dust particle inspection method according to the present invention, there may be further included a step of scanning the region of the article, where any abnormal light intensity of the reflected and diffracted laser beam has been found on the surface of the article as a result of the foregoing scanning with the laser beam having a wavelength $\lambda$ and a coherence distance longer than 1 km, with another laser beam having a coherence distance shorter than 1 km. In this case, the laser beam having a coherence distance shorter than 1 km may be either the laser beam emitted from the LD-excited solid-state laser or the one emitted from the second harmonics generator.

In the dust particle inspection apparatus and method of the present invention, the article to be inspected is irradiated with a laser beam having a high coherence, so that any dust particle or the like existent on the surface of the article can be detected with high precision. Moreover, since the atmosphere surrounding the article placed for inspection is a high-purity inert gas atmosphere, it becomes possible to suppress the occurrence of a speckle pattern.

In a further preferred aspect of the dust particle inspection method according to the present invention, there may be additionally included a step of scanning the region of the article, where any abnormal light intensity of the laser beam reflected and diffracted on the surface of the article has been found, with another laser beam having a different wavelength $\lambda'$ and a coherence distance longer than 1 km. When a fixed relationship dependent on the wavelengths exists between the diffraction angle $\theta$ of the diffracted beam obtained with the wavelength $\lambda$ and the diffraction angle $\lambda'$ of the diffracted beam obtained with the wavelength $\lambda'$, i.e., when the diffracted beams having a relationship of $d \cdot \sin \theta = n\lambda$, $d \cdot \sin \theta' = n\lambda'$ are detected by the optical detector, it is possible to decide with facility the presence of any dust particle in the scanned region. In the above, n denotes the degree (1, 2, . . . ) of the diffracted beam, and d denotes the pitch of a diffraction lattice formed by the dust particle.

Although a higher precision is attainable in detection of a dust particle by the use of a laser beam having a longer coherence distance, there may be induced an increase of the noise component. Meanwhile, if a laser beam having a shorter coherence distance is used, the noise component can be reduced although the precision in detecting a dust particle is lowered. According to a further preferred aspect of the dust particle inspection method of the invention, another laser beam having a shorter coherence distance is employed to scan the region of the inspected article where any abnormal light intensity of the reflected and diffracted beam on the surface of the article has been found. Therefore, by a comparison between the result of scanning with one laser beam of a longer coherence distance and the result of scanning with another laser beam of a shorter coherence distance, the noise component in the scanning result with the laser beam of a longer coherence distance can be eliminated to thereby realize an easy decision of the presence or absence of any dust particle.

The above and other features and advantages of the present invention will become apparent from the following description which will be given with reference to the illustrative accompanying drawings.

DETAILED DESCRIPTION OF THE PREFERRED EMBODIMENTS

Hereinafter the present invention will be described in detail with reference to its preferred embodiments shown in the accompanying drawings. In the following embodiments, it is defined that an article to be inspected is a reticle, and an apparatus and a method for inspection of a dust particle are specifically those for inspection of a dust particle on a reticle.

Figure 1A:
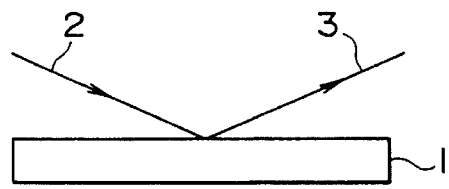
FIGS. 1A to 1C typically illustrate the diffusion and diffraction of a laser beam caused by the presence and absence of a dust particle, and also the angle of irradiation of a laser beam to a reticle.
Figure 1B:
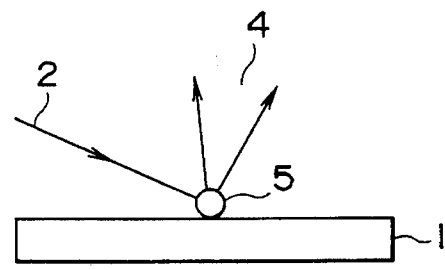
Figure 1C:
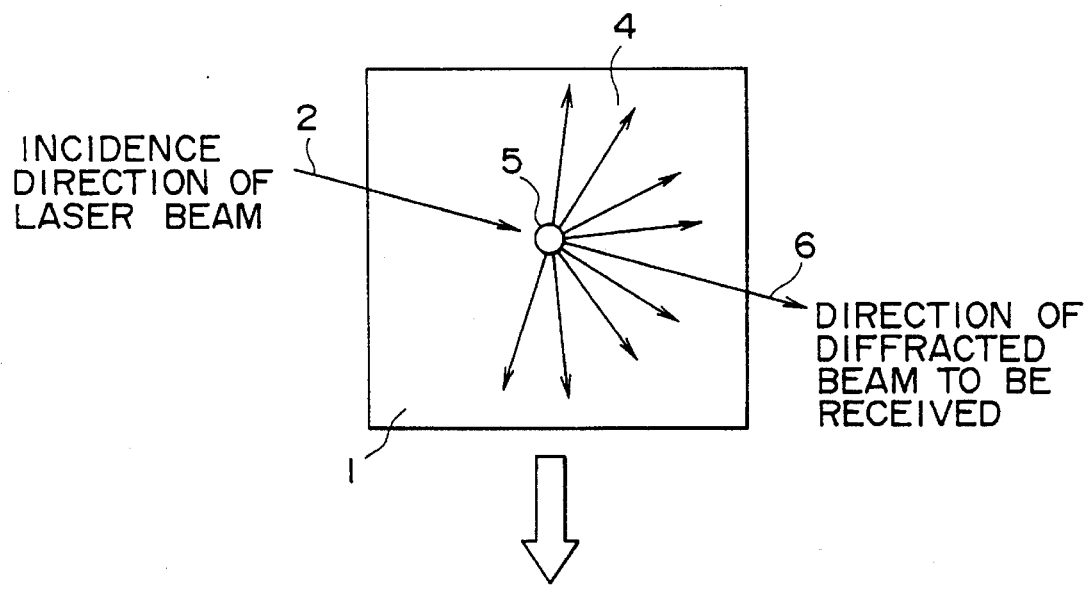
Figure 2:
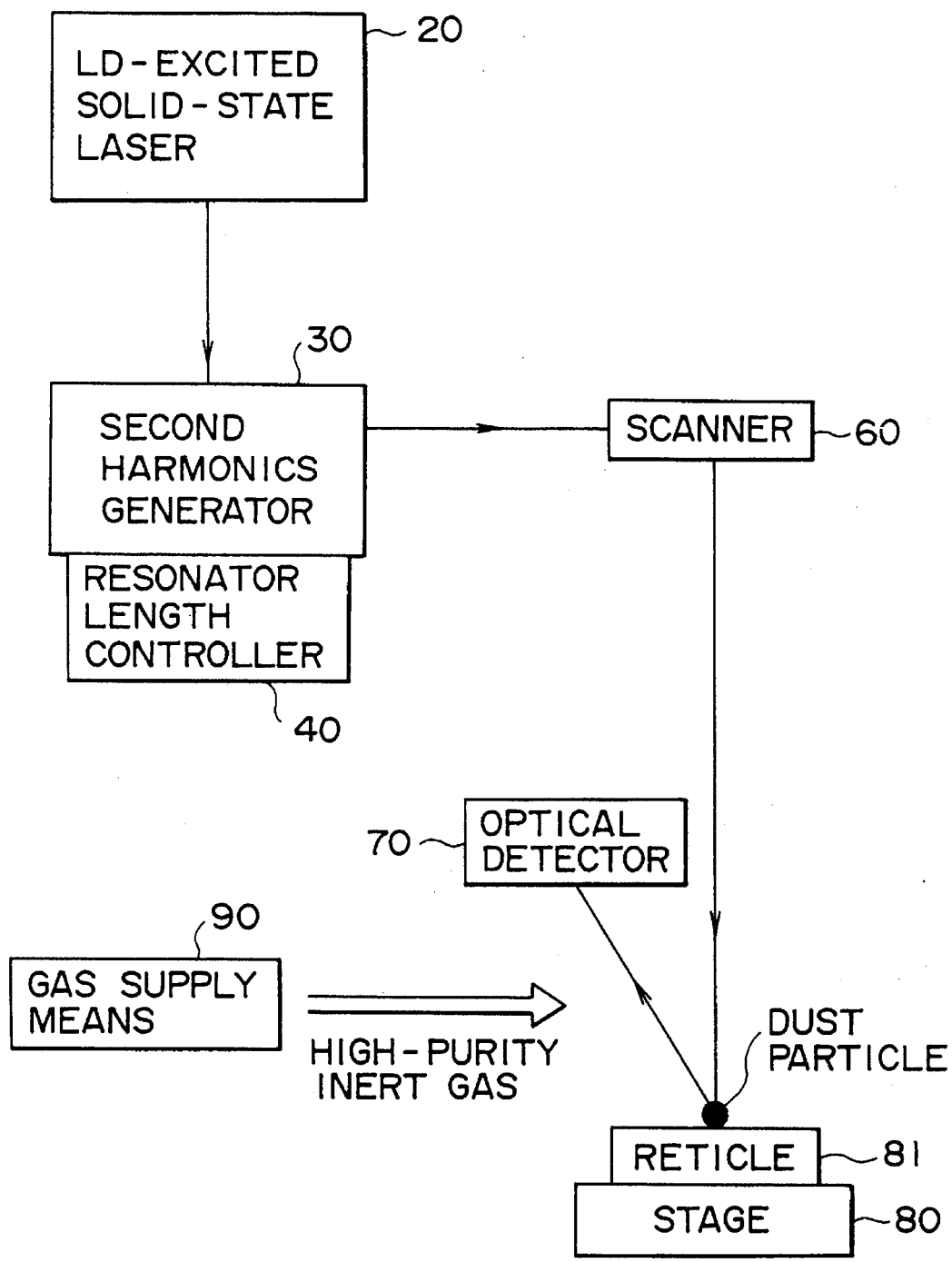
FIG. 2 shows the principle of a dust particle inspection apparatus in a first embodiment of the present invention.
Figure 3:
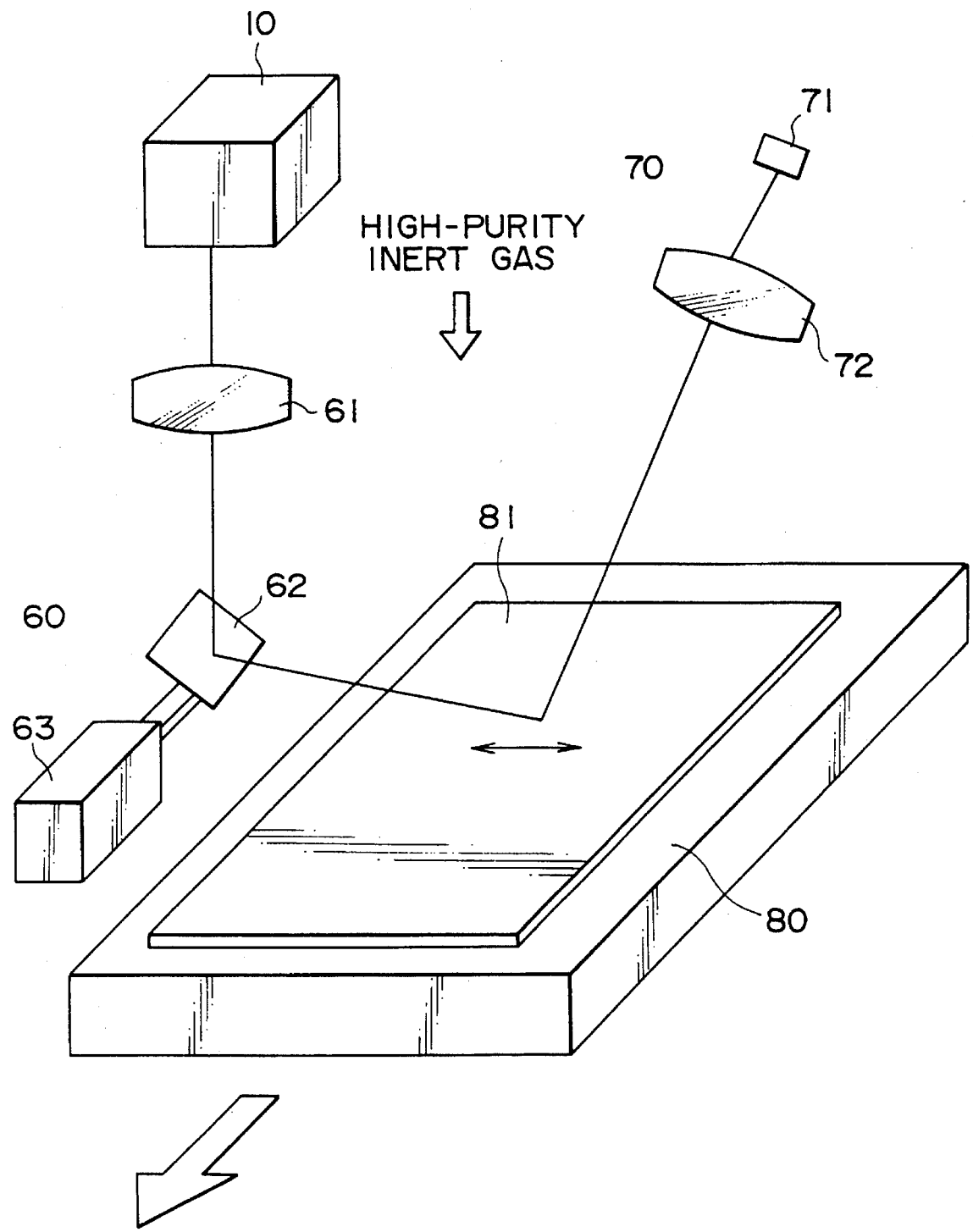
FIG. 3 schematically illustrates the construction of the dust particle inspection apparatus in the first embodiment.

FIG. 2 shows the principle of a dust particle inspection apparatus in a first embodiment of the invention, and FIG. 3 schematically illustrates its construction. The dust particle inspection apparatus in the first embodiment comprises a laser beam source 10; a scanner 60 for scanning the surface of an article, which is to be inspected, with a laser beam emitted from the laser beam source 10; an optical detector 70 for detecting the laser beam reflected and diffracted on the surface of the article; a stage 80 for setting thereon a reticle 81 which is the article to be inspected, and displacing the reticle 81 in a predetermined direction; and a gas supply means 90 for surrounding the reticle 81 with a high-purity inert gas atmosphere. It is preferred that a nitrogen gas having a purity of 99.999% or more be used as the high-purity inert gas. The entire component devices except the laser beam source 10 are incorporated in a housing (not shown) of the dust particle inspection apparatus, and the reticle 81 to be inspected is surrounded With a high-purity inert gas atmosphere as the housing is filled with such high-purity inert gas. The gas supply means 90 may consist of known devices including a high-purity inert gas source, a pipe, a valve and a flow meter. The scanner 60 may comprise, for example, a condenser lens 61, a scanning element 62 consisting of a mirror, and a scanner driver 63. The incidence angle and the emission angle of a laser beam outputted from the scanning element 62 to the condenser lens 61 can be changed by means of the scanner driver 63, whereby the surface of the reticle 81 to be inspected is scanned with the laser beam. It is to be noted that the scanner 60 may comprise a polygon mirror and an f-θ lens as well. The laser beam emitted from the scanning element 62 of the scanner 60 is caused to be incident upon the reticle 81 at an oblique incidence angle. The reticle 81 is irradiated with the laser beam in such a manner that the irradiation direction of the laser beam to the reticle 81 forms a fixed angle α, e.g. 75°, with the displacement direction (Y-direction) of the reticle 81.

The optical detector 70 comprises a photo sensor 71 and a condenser lens 72. Both of the condenser lens 72 and the photo sensor 71 are so disposed as to receive merely the partial diffracted beam in the direction of the aforesaid fixed angle α, whereby the pattern and the dust particle on the reticle 81 can be severely distinguished from each other.

At the time of inspecting the dust particle, the stage 80 for setting the reticle 81 thereon is displaced in a predetermined direction (Y-direction) by a stage shifter (not shown) which is constituted by a combination of a pulse motor and a ball screw for example.

Controlling and measuring circuits(not shown) including a CPU are incorporated to perform various operations of displacing the stage 81, controlling the scanner driver 63, recognizing the laser-beam irradiated position on the reticle 81, processing the output signal from the photo sensor 71, detecting the dust particle and displaying the position thereof on the basis of the laser-beam irradiated position or the output signal from the photo sensor 71.

Figure 4:
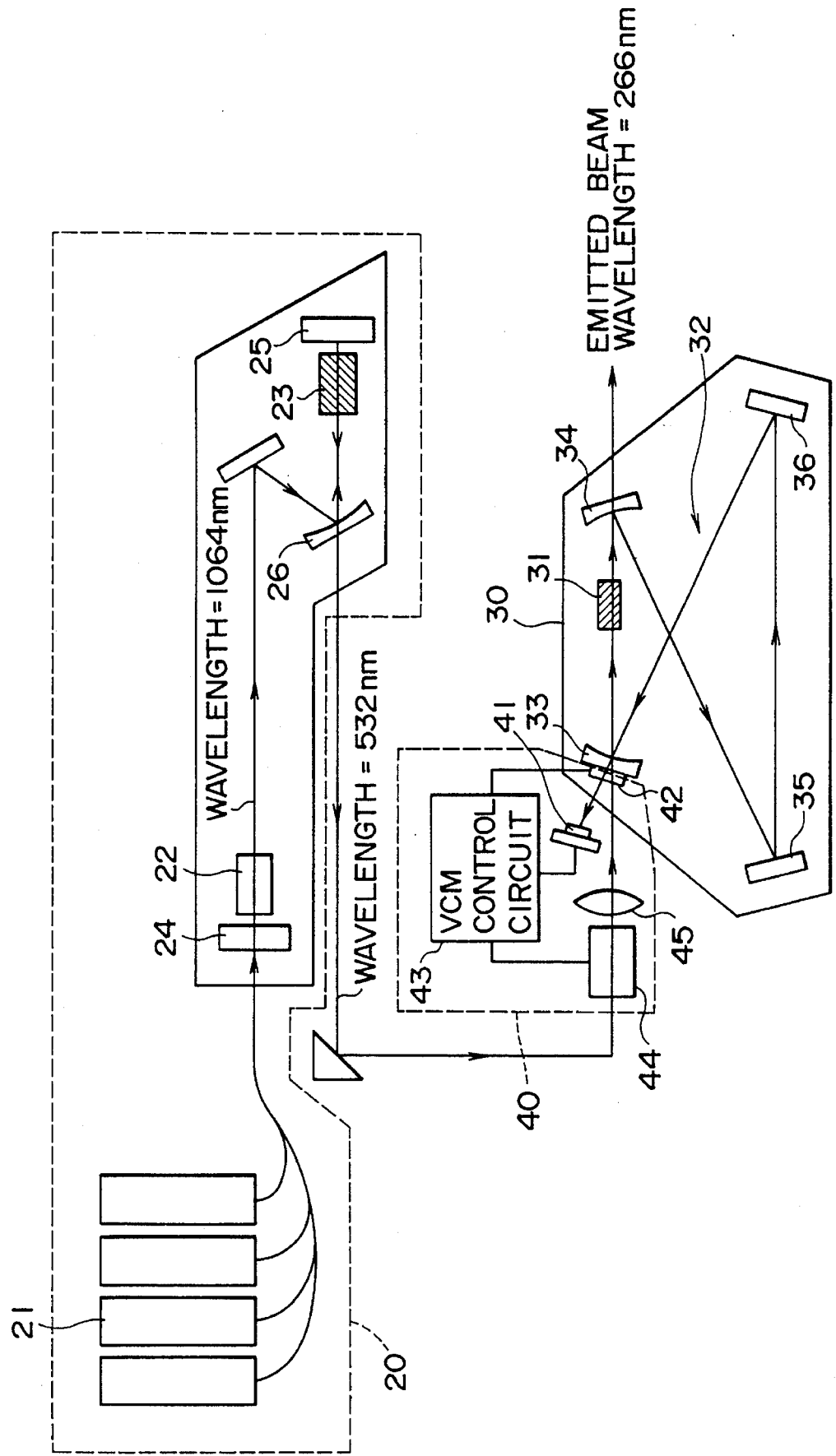
FIG. 4 is a schematic diagram typically showing a laser beam source adapted for use in the dust particle inspection apparatus of the first embodiment.

The laser beam source 10 emits therefrom a laser beam having a coherence distance longer than 1 km. In the first embodiment, the laser beam source 10 comprises an LD-excited solid-state laser 20, a second harmonics generator 30 and a resonator length controller 40. As shown in FIG. 4, the LD-excited solid-stage laser 20 consists of a laser diode 21, a solid-state laser medium 22 composed of Nd:YAG, and a nonlinear optical crystal element 23, and emits second harmonics of the laser beam outputted from the solid-state laser medium 22. Meanwhile the second harmonics generator 32 consists of a nonlinear optical crystal element 31 and an optical resonator 32. The resonator length controller 40 is provided for controlling the resonance length of the optical resonator 32. The light beam emitted from the LD-excited solid-state laser 20 is caused to be incident upon the second harmonics generator 30, and the light beam of a wavelength based on the second harmonics of the incident beam is emitted from the second harmonics generator 30. The details of the laser beam source 10 will be described later.

The dust particle inspection apparatus of the first embodiment is used normally in combination with a reticle changer. Inspection of each reticle is performed by the dust particle inspection apparatus when the reticle is forwarded from a reticle cassette housing carrier of a reticle changer to a predetermined position in a semiconductor exposer or when the reticle is returned therefrom.

In carrying the dust particle inspection method of the first embodiment into effect, initially the reticle 81 to be inspected is set on the stage 80 by the use of an unshown reticle changer, and then a high-purity inert gas is supplied from the gas supply means 90 to thereby surround the reticle 81 with a high-purity inert gas atmosphere. Subsequently the stage 80 is displaced by a stage shifter so that the reticle 81 to be inspected is displaced in a predetermined direction (Y-direction). Simultaneously the surface of the reticle 81 is scanned, by means of the scanner 60, with a laser beam emitted from the laser beam source 10 and having a wavelength λ (e.g. 266 nm) and a coherence distance longer than 1 km. Thereafter the laser beam reflected and diffracted on the surface of the reticle 81 is detected by the optical detector 70, and the dust particle existing on the surface of the reticle 81 is detected in accordance with a signal outputted from the optical detector 70.

FIG. 4 is a detailed block diagram of the preferred laser beam source 10 employed in the dust particle inspection apparatus of the first embodiment. As shown in this diagram, the laser beam source 10 in the first embodiment consists of an LD-excited solid-state laser 20 which is capable of emitting second harmonics therefrom. More specifically, the LD-excited solid-state laser 20 comprises a plurality of laser diodes 21 (output beam wavelength: 808 nm), a solid-state laser medium 22 (output beam wavelength: 1064 nm) composed of Nd:YAG, and a nonlinear optical crystal element 23 composed of KTP (KTiOPO4). The solid-state laser medium 22 is of an end face excitation type. As a consequence of the structure mentioned above, a laser beam of 532 nm corresponding to the second harmonics from the solid-state laser medium 22 of Nd:YAG is emitted from the LD-excited solid-state laser 20. In this solid-state laser 20, a ¼ wavelength plate 24 is disposed in front of the solid-state laser medium 22 composed of Nd:YAG. Consequently it is rendered possible in the LD-excited solid-state laser 20 to suppress multi-mode oscillation that may be caused by the Hall burning effect.

The nonlinear optical crystal element 23 is disposed in the optical path of an optical resonator consisting of a plane mirror 25 and a concave mirror 26, and constitutes an external SHG system (where the nonlinear optical crystal element is disposed in an optical resonator positioned outside a laser oscillator). The plane mirror 25 reflects almost the entire laser beam therefrom, while the concave mirror 26 transmits therethrough almost the entire second harmonics outputted from the solid-state laser medium 22 of Nd:YAG but reflects almost the entire laser beam of any other wavelength. The concave mirror 26 may consist of a dichroic mirror for example.

As shown in FIG. 4, the second harmonics generator 30 comprises a nonlinear optical crystal element 31 composed of, e.g. BBO (β-BaB2O4) and an optical resonator 32. In the first embodiment, the nonlinear optical crystal element 31 constituting the second harmonics generator 30 is disposed in the optical path of the optical resonator 32. Namely, the second harmonics generator 30 is of an external SHG type. In the optical resonator 32, the nonlinearity effect of the nonlinear optical crystal element 31 disposed in the optical resonator 32 can be effectively utilized by increasing the finesse value (corresponding to the Q value of resonance) to a range of 100 to 1000 or so and raising the optical density in the optical resonator 32 several hundred times the optical density of the laser beam incident upon the optical resonator 32.

The optical resonator 32 comprises a pair of concave mirrors 33, 34 and a pair of plane mirrors 35, 36. The laser beam (having a wavelength of, e.g., 532 nm) incident upon the second harmonics generator 30 is transmitted successively through the first concave mirror 33 and the nonlinear optical crystal element 31 to be thereby converted at least partially into a second harmonic beam (having a wavelength of, e.g., 266 nm). Subsequently such a second harmonic beam is reflected by the second concave mirror 34 and the plane mirrors 35, 36 in this order, and then is further reflected by the first concave mirror 33. In this state, the laser beam (having a wavelength of, e.g., 266 nm) incident upon the second concave mirror 34 is passed therethrough at least partially and then is emitted from the second harmonics generator 30 toward the scanner 60. A portion of the beam (having a wavelength of, e.g., 532 nm) reflected from the plane mirror 36 and caused to be incident upon the first concave mirror 33 is transmitted through the first concave mirror 33 and then is incident upon the undermentioned resonator length controller 40. The first and second concave mirrors 33, 34 and plane mirrors 35, 36 are so designed as to reflect and transmit the laser beam in the manner described above. The second concave mirror 34 may consist of a dichroic mirror for example.

With reference to the input laser beam incident upon the second harmonics generator 30, the wavelength of the output beam emitted from the second harmonics generator 30 corresponds to second harmonics of the incident input beam. More specifically, in the first embodiment, the wavelength of the input beam incident upon the second harmonics generator 30 from the LD-excited solid-state laser 20 is 532 nm, and the wavelength of the output beam emitted from the second harmonics generator 30 is 266 nm. With reference to the wavelength (1064 nm) of the laser beam emitted from the solid-state laser medium 22 of Nd:YAG, the output beam obtained from the second harmonics generator 30 corresponds to fourth harmonics. A laser beam having a narrow band of a wavelength 266 nm is emitted continuously from the second harmonics generator 30, and the mode uniformity of such a laser beam is high.

The resonator length (L) of the optical resonator 32 is controlled precisely by means of the resonator length controller 40 to be thereby retained at a fixed value. With such precise retention of the resonator length (L) of the optical resonator 32 at a fixed value, it becomes possible to maintain constant the intensity of the output beam emitted from the second harmonics generator 30. The resonator length (L) corresponds to the length of the optical path which connects the respective reflecting surfaces of the first concave mirror 33, the second concave mirror 34, the plane mirrors 35 and 36, and the first concave mirror 33. When the resonator length Lo of the optical resonator 32 satisfies the condition of $\lambda = Lo/M$ (where M is a positive integer) in a locked state relative to the wavelength μ of the output beam emitted from the second harmonics generator 30, the optical resonator 32 resonates and emits a high-intensity beam stably. In other words, when the optical-path phase difference Δ in the optical resonator 32 is an integral multiple of $2\pi$, the optical resonator 32 constituting the second harmonics generator 30 is placed in a state of resonance, i.e., a locked state. Relative to the refraction factor n of the nonlinear optical crystal element 31 and the thickness 1 thereof, the optical-path phase difference α can be expressed as $(4\pi nl/\lambda)$.

Meanwhile when the resonator length $Lo \pm \Delta Lo$ of the optical resonator 32 is $\lambda = (Lo \pm \Delta Lo)/M'$ (where M' is a positive integer) in an unlocked state, the second harmonics generator 30 emits a low-intensity beam. In other words, when the optical-path phase difference Δ has any deviation from an integral multiple of $2\pi$, the optical resonator 32 constituting the second harmonics generator 30 is placed in a state of non-resonance, i.e., an unlocked state.

Accordingly, for achieving stable emission of the beam of the wavelength λ from the second harmonics generator 30, it is necessary to minimize the temporal variation in the resonator length (L) of the optical resonator 32 (specifically, for example, the positional variations of the concave mirrors 33, 34 and the plane mirrors 35, 36). For this reason, the first concave mirror 33 is positionally shifted on the optical axis connecting the first concave mirror 33 and the second concave mirror 34 under control of the resonator length controller 40, or the angle of disposition of the first concave mirror 3 to the same optical axis is changed under such control to suppress the temporal variation in the resonator length (L) of the optical resonator 32, thereby maintaining constant the resonator length (L) of the optical resonator 32.

Regarding the resonance length controller 40 employed in the first embodiment mentioned, there is a detailed description in "Laser Beam Generator" (Japanese Patent Laid-open No. Hei 5 (1993)-243661) filed by the present applicant on Mar. 2, 1992.

As shown in FIG. 4, the resonator length controller 40 of the above type comprises an optical detector 41 such as a photo diode, a voice coil motor (VCM) 42, a voice coil motor control circuit (VCM control circuit) 43, and a phase modulator 44. The phase modulator 44 is disposed in the optical path between the LD-excited solid-state laser 20 and the second harmonics generator 30, and consists of an EO (electro-optical) element or an AO (acousto-optical) element for effecting phase modulation of the beam emitted from the LD-excited solid-state laser 20. A condenser lens 45 is disposed between the phase modulator 44 and the second harmonics generator 30. Then the first concave mirror 33 constituting the optical resonator 32 is attached to the voice coil motor 42.

Figure 5:
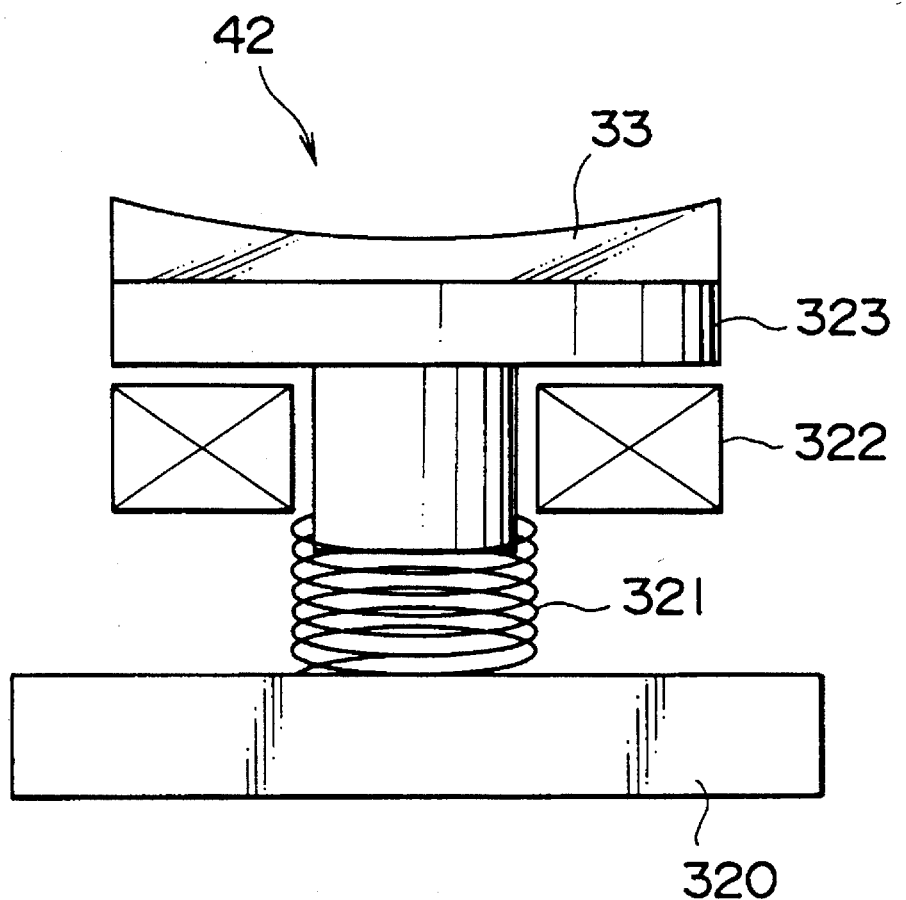
FIG. 5 typically shows the structure of a voice coil motor.

As typically illustrated in FIG. 5, the voice coil motor 42 is an electromagnetic actuator comprising a base 320 composed of a magnetic material, one or more electromagnets (voice coils) 322, a yoke 323 composed of a magnetic member, and at least one coil spring (or spiral leaf spring) 321. One end of the coil spring 321 is anchored to the base 320, while the other end thereof is anchored to the yoke 323. And the first concave mirror 23 and the electromagnet 322 are attached to the yoke 323. When a current is caused to flow in the electromagnet 322, a magnetic field is formed to thereby change the distance between the yoke 323 and the base 320. As a result, the first concave mirror 33 can be positionally shifted. More specifically, the resonator length (L) of the optical resonator 32 is changeable by controlling the current which flows in the electromagnet 322. Thus, a servo control action is executed for the voice coil motor 42.

The current required for driving the voice coil motor 42 ranges from several ten to several hundred mA. Therefore the driving circuit can be produced at a low cost. Further the double resonance frequency of the servo loop can be set at several ten to one hundred kHz or more and, due to the frequency characteristics with a minimal phase shift, it is possible to widen the servo band to several ten MHz, hence realizing a stable control action.

When the optical resonator 32 is in its locked state, the intensity of the beam obtained from the first concave mirror 33 for example and arriving at the optical detector 41 is rendered minimum and the phase of such beam is greatly varied. The technique of controlling the optical resonator by utilizing such variation is disclosed in, e.g., R. W. P. Drever, et al., "Laser Phase and Frequency Stabilization Using an Optical Resonator", Applied Physics B31, 97–105 (1983). Controlling the locked state of the optical resonator 32 is performed fundamentally by applying the above technique.

More specifically, if the first concave mirror 33 is positionally shifted by driving the voice coil motor 42 by means of the VCM control circuit 43 in such a manner that the intensity of the beam transmitted through the first concave mirror 33 for example and arriving at the optical detector 41 is retained at its minimum value (e.g., zero), it is possible to stably maintain the optical resonator 32 in the locked state. In other words, a detection signal is obtained by first phase-modulating the output beam of the LD-excited solid-state laser 20 in accordance with a phase modulation signal, then causing the modulated beam to be incident upon the second harmonics generator 30, and detecting the return beam from the second harmonics generator 30 by the optical detector 41. Thereafter the detection signal thus obtained is synchronously detected by using the phase modulation signal to thereby extract an error signal. The voice coil motor 42 is driven by the VCM control circuit 43 so that the error signal becomes zero, whereby the first concave mirror 33 is positionally shifted.

Figure 6:
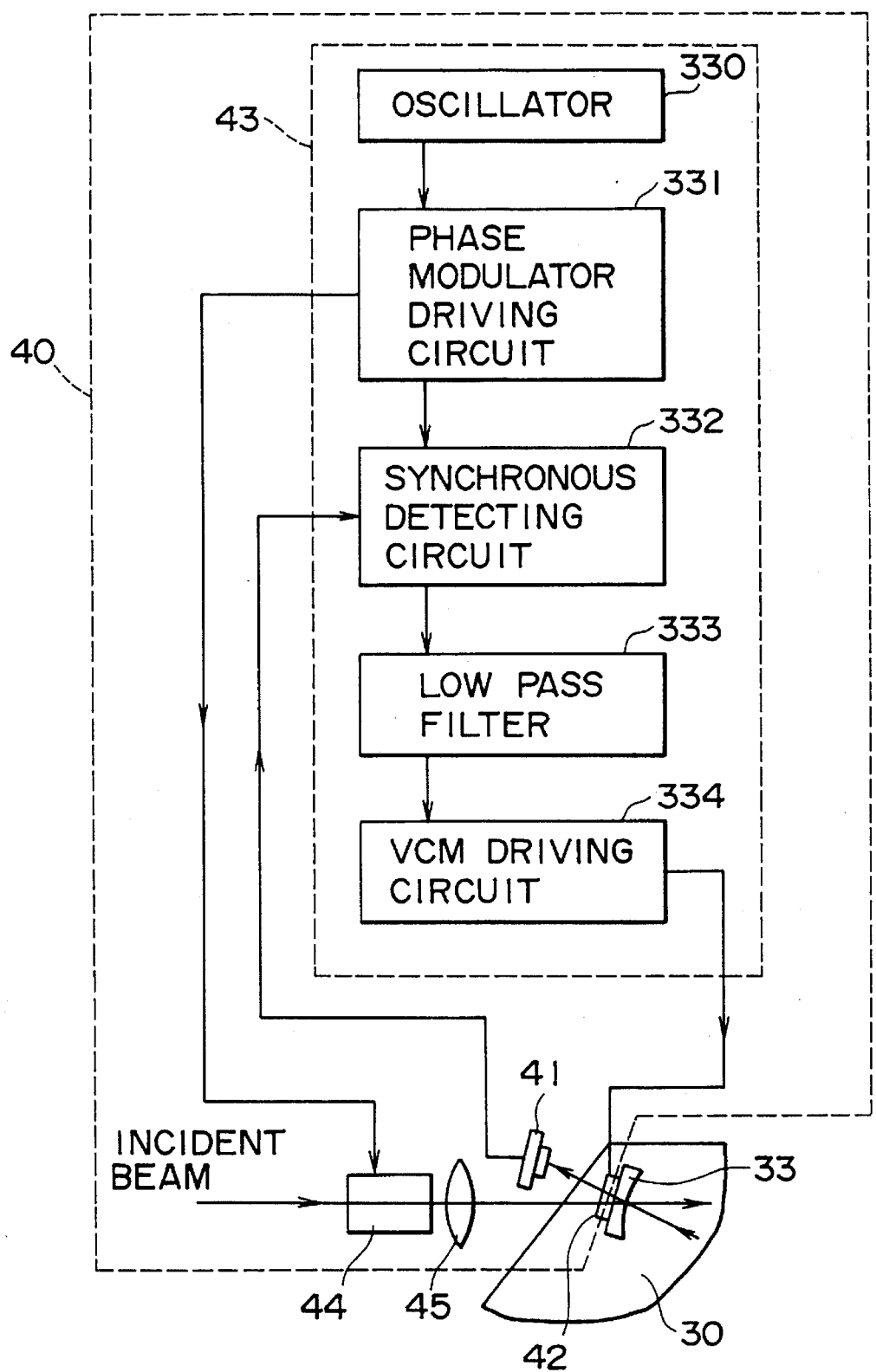
FIG. 6 is a block diagram of a VCM control circuit constituting a resonator length controller.

As shown in a block diagram of FIG. 6, the VCM control circuit 43 comprises, for example, an oscillator 330, a phase-modulator driving circuit 331, a synchronous detecting circuit 332, a low pass filter 333 and a voice coil motor driving circuit (VCM driving circuit) 334.

A modulation signal of a frequency fm (e.g. 10 MHz) outputted from the oscillator 330 is supplied to the phase modulator 44 via the phase-modulator driving circuit 331. Then in the phase modulator 44, the beam (of a frequency fo on the order of 1014 Hz) emitted from the LD-excited solid-state laser 20 is phase-modulated to form sidebands of frequencies fo±fm.

The beams (of frequencies fo and fo±fm) emitted to the outside of the optical system of the resonator 32 through the first concave mirror 33 constituting the optical resonator 32 are detected by the optical detector 41. A polar error signal can be obtained according to the FM sideband process which detects the beat between the beams having such frequencies (fo and fo±fm), and the resonator length (L) of the optical resonator 32 is controlled on the basis of the error signal thus obtained.

The signal outputted from the optical detector 41 is supplied to the synchronous detecting circuit 332. This output signal is composed of the beam intensity signal of the frequency fo and the signal superimposed thereon and corresponding to the modulation signal of the frequency fm. To the synchronous detecting circuit 332, there is also supplied the modulation signal outputted from the oscillator 330 and processed, when necessary, in waveform shaping and phase delay stages. The output signal from the optical detector 41 is multiplied by the modulation signal in the synchronous detecting circuit 322, where synchronous detection is then performed. The detection output signal obtained from the synchronous detecting circuit 332 is supplied to the low pass filter 333, where the modulation signal component is eliminated from the detection output signal to thereby produce an error signal which relates to the resonator length of the optical resonator 32. This error signal represents the difference (±ΔLo) between the preset resonator length (Lo) of the optical resonator 32 and the measured resonator length (Lo±ΔLo).

Subsequently the error signal is supplied to the VCM driving circuit 334, so that the voice coil motor 42 is driven in accordance with the error signal (specifically the current flowing in the electromagnet 322 is controlled), whereby the resonator length (L) of the optical resonator 32 is adjusted in such a manner that the beam transmitted through the first concave mirror 33 and arriving at the optical detector 41 is minimized (in other words, the resonator length of the optical resonator 32 is regulated to Lo and the error signal is reduced to zero).

When the resonator length (L) of the optical resonator 32 is set to Lo (i.e., in a locked state), any temporal variation in the resonator length (L) of the optical resonator 32 (specifically, the positional variations of the concave mirrors 33, 34 and the plane mirrors 35, 36 for example) can be suppressed, under control of the resonator length controller 40, within a range of 1/1000 to 1/10000 of the beam incident upon the second harmonics generator 30.

Figure 7:
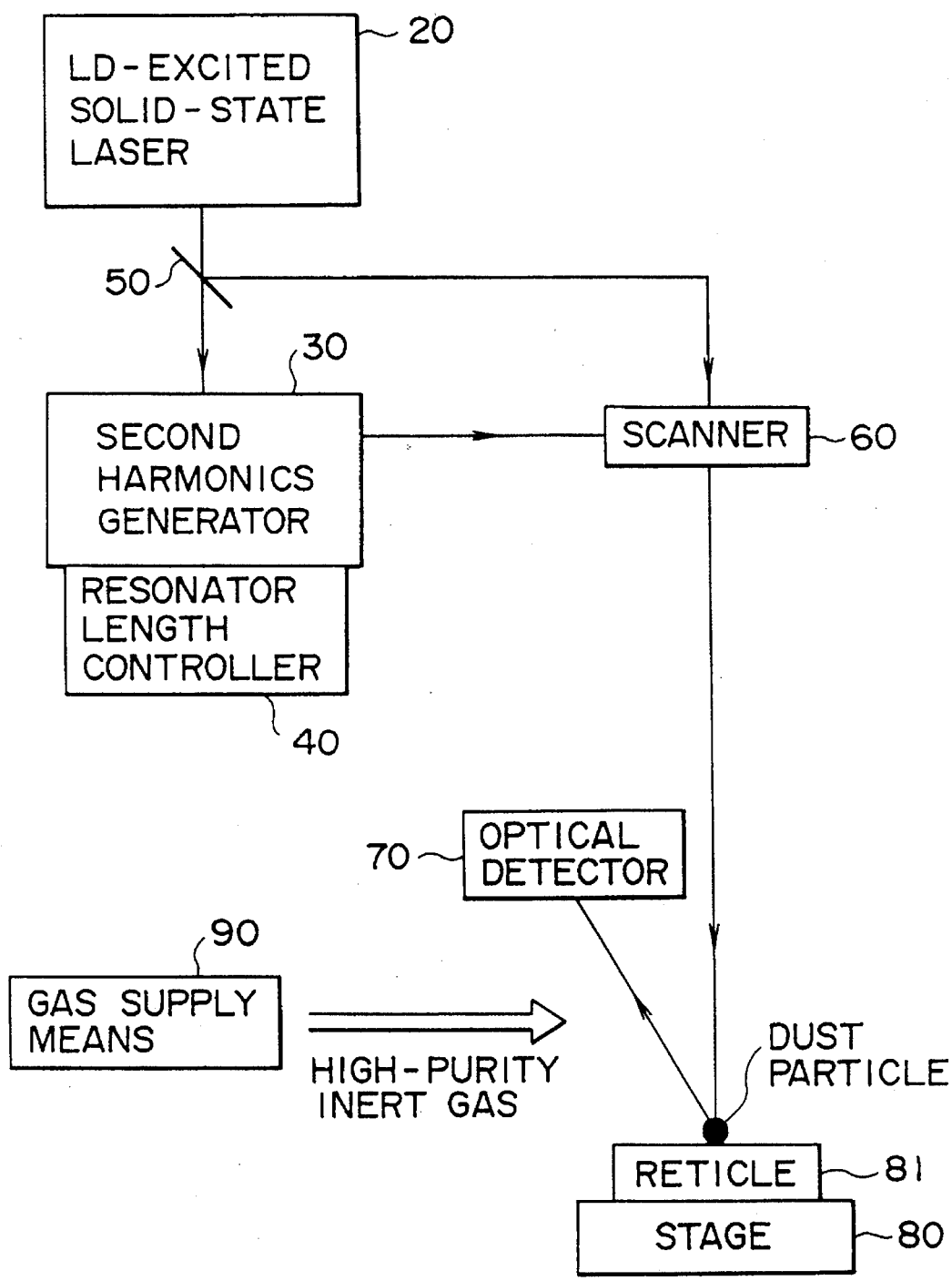
FIG. 7 shows the principle of a dust particle inspection apparatus in a second embodiment of the invention.

FIG. 7 shows the principle of a second embodiment according to the present invention. In this embodiment, a laser beam source 10 is equipped with an optical path split means 50 for partially causing the laser beam, which is emitted from an LD-excited solid-state laser 20, to be incident upon a scanner 60. The optical path split means 50 may comprise, for example, a half mirror, a beam splitter and a quadrangular pyramid. Meanwhile the remaining portion of the laser beam emitted from the LD-excited solid-state laser 20 is caused to be incident upon a second harmonics generator 30. Since the other construction of the dust particle inspection apparatus is the same as that of the foregoing first embodiment, a detailed description thereof is omitted here.

In carrying the dust particle inspection method of the second embodiment into effect, initially the reticle 81 to be inspected is set on the stage 80 by the use of a reticle changer(not shown), and then a high-purity inert gas is supplied from the gas supply means 90 to thereby surround the reticle 81 with a high-purity inert gas atmosphere. Subsequently the stage 80 is displaced by a stage shifter so that the reticle 81 to be inspected is displaced in a predetermined direction (Y-direction). Simultaneously the surface of the reticle 81 is scanned, by means of the scanner 60, with a laser beam emitted from the laser beam source 10 and having a wavelength λ (e.g. 532 nm) and a coherence distance longer than 1 km. This laser beam is the one emitted initially from the LD-excited solid-state laser 20 and then split by the optical path split means 50. The beam reflected and diffracted on the surface of the reticle 81 is detected by the optical detector 70. The region of the reticle 81 being inspected, where any abnormal beam intensity has been found, is specified in accordance with the signal outputted from the optical detector 70. There is a relationship of d·sinθ=nλ between the diffraction angle θ and the wavelength λ of the diffracted beam obtained in this reticle region. In the above equation, n denotes the degree (1, 2, . . . ) of the diffracted beam, and d denotes the pitch of a diffraction lattice formed by the dust particle.

Upon completion of the serial inspection of the reticle 81 being inspected or upon discovery of any abnormal beam intensity, the region of the reticle 81 with such abnormal beam intensity is immediately inspected again. In this case, the relevant region is scanned with a laser beam emitted from the second harmonics generator 30 and having a wavelength λ' of 266 nm and a coherence distance longer than 1 km. When any dust particle is existent in this region, a diffracted beam is obtained from this region and there is a relationship of d·sinθ'=nλ' between the diffraction angle θ' and the wavelength λ' of the diffracted beam. Meanwhile, in the case where a diffracted beam is obtained in scanning the reticle 81 with one beam of the wavelength λ but none of such diffracted beam is obtained in scanning the reticle 81 with another beam of the wavelength λ', it is possible to decide that the diffracted beam obtained in scanning the reticle 81 with one beam of the wavelength λ is a kind of noise. Therefore the presence or absence of any dust particle on the reticle under inspection can be discriminated with facility.

Figure 8:
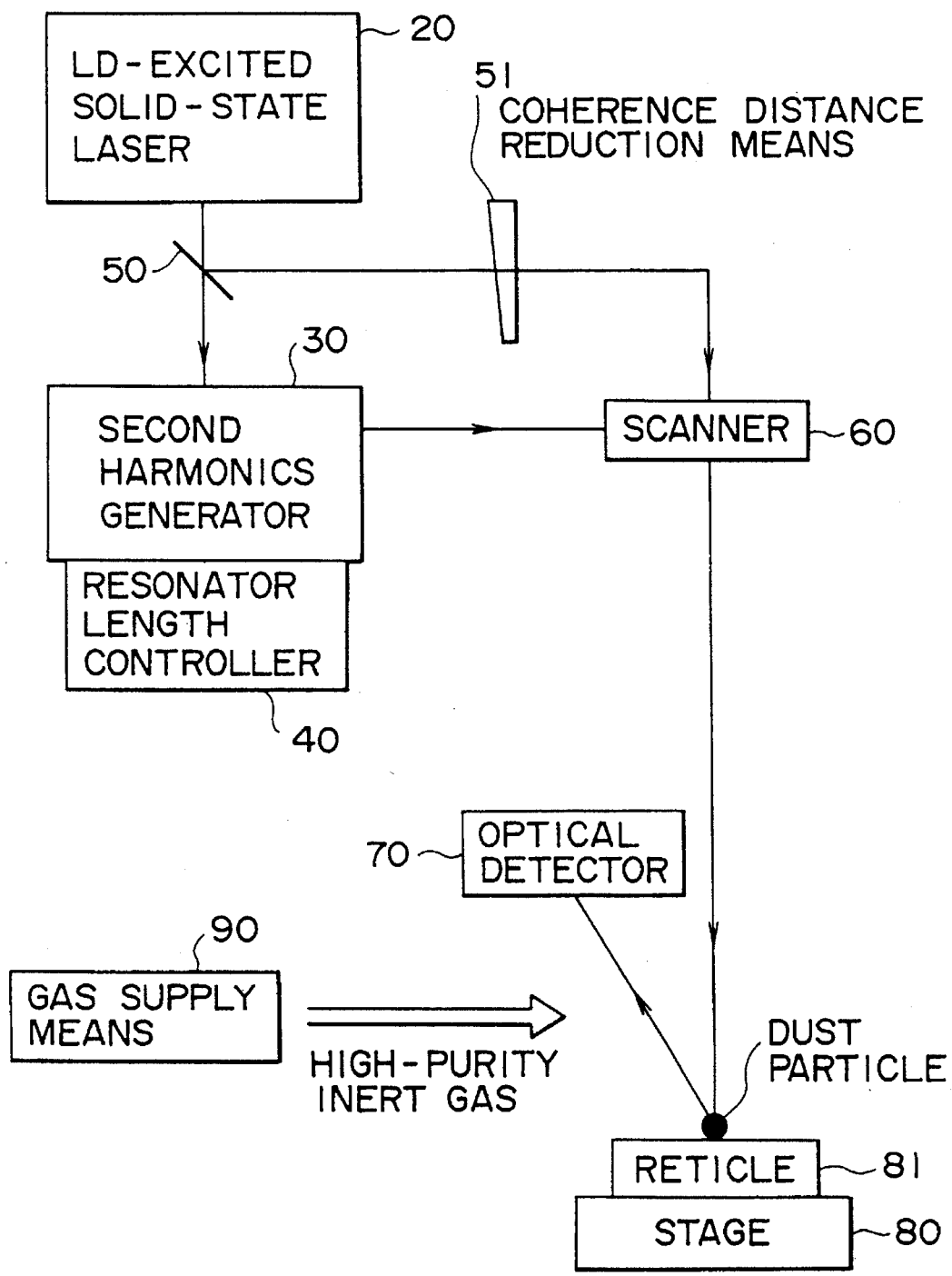
FIG. 8 shows the principle of a dust particle inspection apparatus in a third embodiment of the invention.

FIG. 8 shows the principle of a third embodiment according to the present invention. A laser beam source 10 is equipped with an optical path split means 50 for partially causing the laser beam, which is emitted from an LD-excited solid-state laser 20, to be incident upon a scanner 60. The optical path split means 50 may comprise, for example, a half mirror, a beam splitter and a quadrangular pyramid. In this third embodiment, a coherence distance reduction means 51 is further provided between the optical path split means and the scanner. The coherence distance reduction means may consist of, for example, a rotary diffuser plate or a frosted glass member. Meanwhile the remaining portion of the laser beam emitted from the LD-excited solid-state laser 20 is caused to be incident upon the second harmonic generator 30. Since the other construction of the dust particle inspection apparatus is the same as that of the aforementioned first embodiment, a detailed description thereof is omitted here.

In carrying the dust particle inspection method of the third embodiment into effect, initially the reticle 81 to be inspected is set on the stage 80 by the use of a reticle changer(not shown), and then a high-purity inert gas is supplied from the gas supply means 90 to thereby surround the reticle 81 with a high-purity inert gas atmosphere. Subsequently the stage 80 is displaced by a stage shifter so that the reticle 81 to be inspected is displaced in a predetermined direction (Y-direction). Simultaneously the surface of the reticle 81 is scanned, by means of the scanner 60, with a laser beam emitted from the laser beam source 10 and having a wavelength λ (e.g. 266 nm) and a coherence distance longer than 1 km. This laser beam is the one emitted initially from the second harmonics generator 30. The beam reflected and diffracted on the surface of the reticle 81 is detected by the optical detector 70. And the region of the reticle 81 being inspected, where any abnormal beam intensity has been found, is specified in accordance with the signal outputted from the optical detector 70. This region is considered to have a high possibility that some dust particle is existent thereon.

Upon completion of the serial inspection of the reticle 81 being inspected or upon discovery of any abnormal beam intensity, the region of the reticle 81 with such abnormal beam intensity is immediately inspected again. The laser beam used in this stage of the operation is the one (wavelength=532 nm) emitted initially from the LD-excited solid-state laser 20 and split by the optical path split means 50 and further processed by the coherence distance reduction means 51 in such a manner that the coherence distance thereof is reduced to be shorter than 1 km. When any dust particle is existent in this region, a diffracted beam is obtained from this region. Meanwhile, in the case where a diffracted beam is obtained in scanning the reticle 81 with one beam of the longer coherence distance but none of such diffracted beam is obtained in scanning the reticle 81 with another beam of the shorter coherence distance, it is possible to decide that the diffracted beam obtained in scanning the reticle 81 with one beam of the longer coherence distance is a kind of noise. Therefore the presence or absence of any dust particle on the reticle under inspection can be discriminated with facility.

Figure 9:
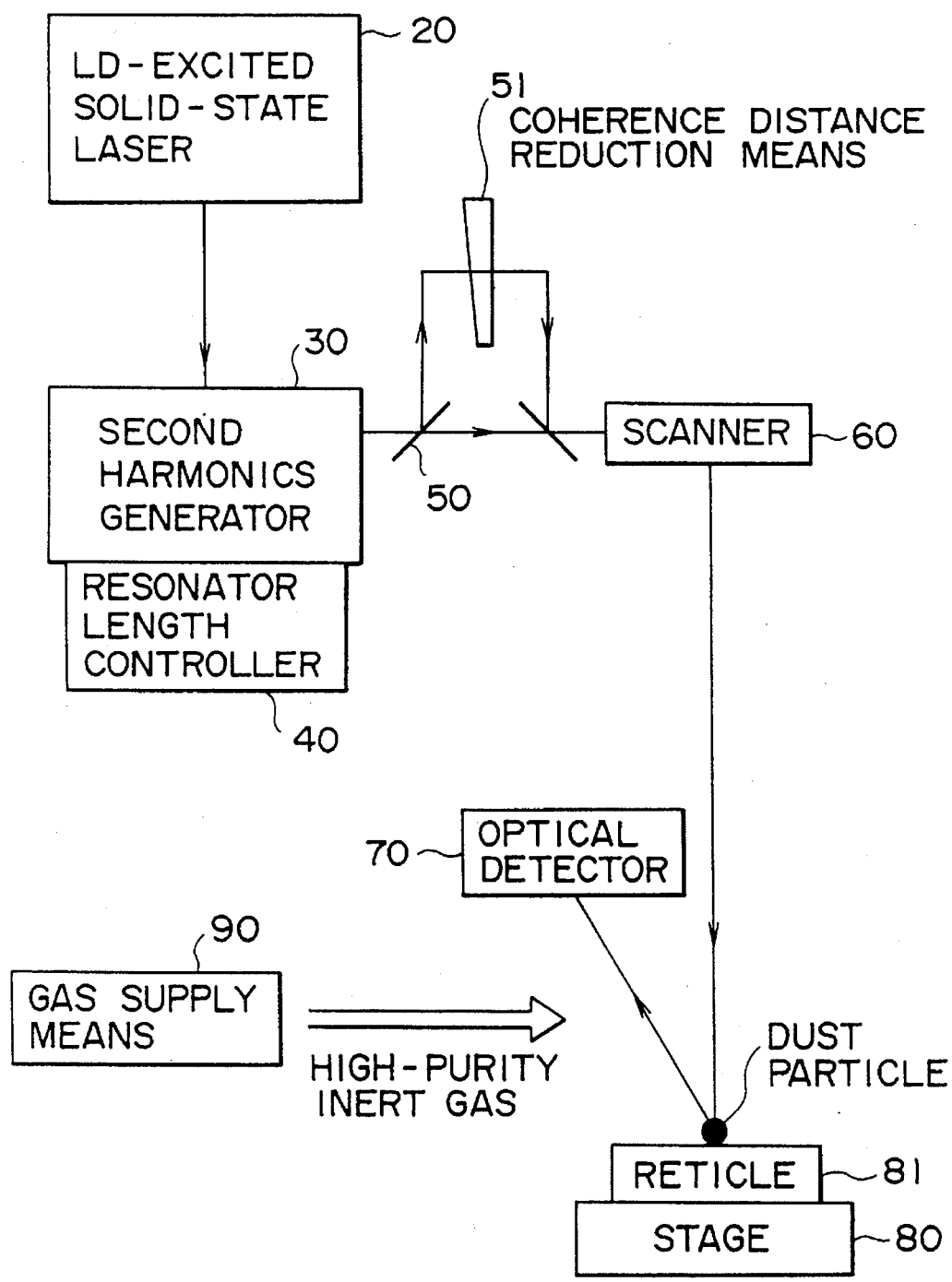
FIG. 9 shows the principle of a dust particle inspection apparatus in a fourth embodiment of the invention.

Now a fourth embodiment of the present invention will be described below with reference to FIG. 9. In this dust particle inspection apparatus, there are included an optical path split means for partially splitting the laser beam emitted from a second harmonics generator 30, and a coherence distance reduction means 51 disposed between such optical path split means 50 and a scanner 60.

Figure 10:
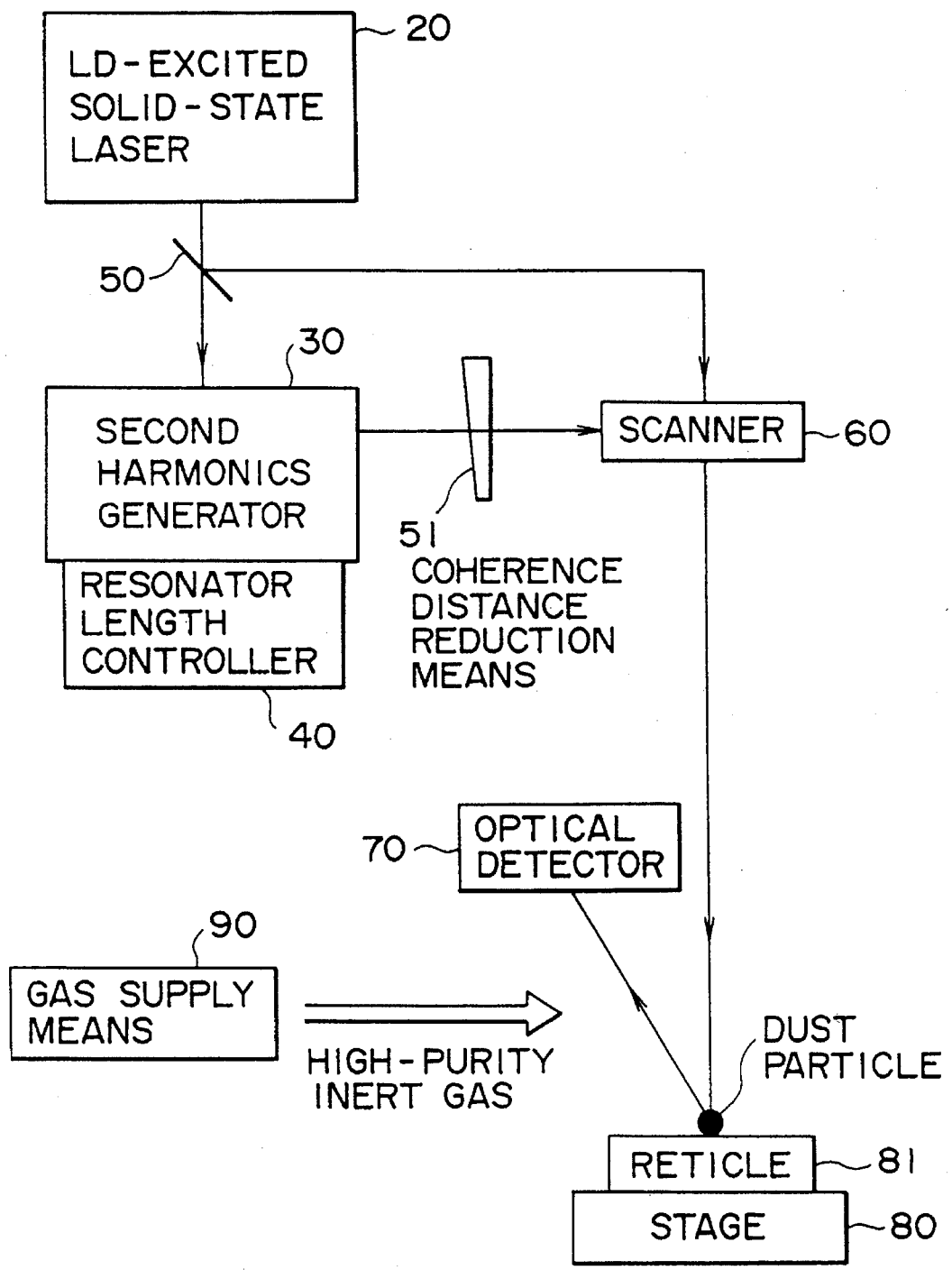
FIG. 10 shows the principle of a dust particle inspection apparatus in a fifth embodiment of the invention.

In a dust particle inspection method carried out by the use of this apparatus, first the laser beam emitted from the second harmonics generator 30 is caused to be incident directly upon the scanner 60 to scan the article under inspection. Thereafter the laser beam emitted initially from the second harmonics generator 30 and processed through the coherence distance reduction means 51 is caused to be incident upon the scanner 60, whereby the article being inspected is scanned again. Hereinafter a fifth embodiment of the present invention will be described with reference to FIG. 10. In this dust particle inspection apparatus, an optical path split means 50 is disposed between an LD-excited solid-state laser 20 and a second harmonics generator 30, and a portion of the laser beam split by the optical path split means 50 is caused to be incident directly upon a scanner 60. Meanwhile a coherence distance reduction means 51 is disposed between the second harmonics generator 30 and the scanner 60.

In a dust particle inspection method carried out by the use of this apparatus, first the laser beam emitted initially from the LD-excited solid-state laser 20 and split by the optical path split means 50 is caused to be incident directly upon the scanner 60 to thereby scan the article under inspection. Thereafter the laser beam emitted from the second harmonics generator 30 and processed through the coherence distance reduction means 51 is caused to be incident upon the scanner 60, whereby the article being inspected is scanned again.

Although the present invention has been described with reference to the preferred embodiments thereof, it is to be noted that the present invention is not limited to such embodiments alone. The respective structures of the LD-excited solid-state laser 20, the second harmonic generator 30 and the resonator length controller 40 are merely illustrative and may be adequately modified in design. The solid-state laser medium may be composed of Nd:YVO4, Nd:BEL or LNP as well in addition to the aforementioned Nd:YAG. The excitation system for the solid-state laser medium by the use of laser diodes is not limited to the exemplary end-face excitation system but may also be a side-face or surface excitation system, and a slab solid-state laser may be employed as well. Further the nonlinear optical crystal element may be selectively composed of LN, QPM LN, LBO, KN or the like besides the aforementioned KTP or BBO, depending on the required wavelength of the incident or emitted laser beam.

In a modification, it is possible to employ an internal SHG type laser beam source where a solid-state laser medium and a nonlinear optical crystal element are disposed in the optical path of an optical resonator consisting of a pair of reflecting mirrors. It is also possible to adopt a modified construction where the beam emitted from the solid-state laser medium 22 is transmitted through the nonlinear optical crystal element 23 (i.e., a construction where the optical resonator consisting of the plane mirror 25 and the concave mirror 26 is omitted). In another modification, a blue semiconductor laser for example may be used as a laser beam source in place of the aforementioned LD-excited solid-state laser, and the beam emitted from such a semiconductor laser may be directly incident upon the second harmonics generator, or the second harmonics generator may be combined with an internal SHG type laser beam source which consists of such a semiconductor laser and a nonlinear optical crystal element. Furthermore, the resonator length controller 40 may be provided separately for controlling the resonator length of the optical resonator which consists of the plane mirror 25 and the concave mirror 26.

Structurally the optical resonator 32 in the second harmonics generator 30 may be of Fabry-Perot type consisting of, e.g., a concave mirror and a plane mirror. In this case, a reflecting mirror capable of transmitting therethrough the beam incident upon the second harmonics generator 30 and reflecting the return beam from the second harmonics generator 30 may be disposed at a position anterior to the second harmonics generator 30, and the beam reflected from such a mirror may be detected by the optical detector 41. For changing the resonator length of the optical resonator 32, the other mirror may be displaced instead of the first concave mirror 33.

In another modification of the resonator length controller 40, it may be composed of PZT or the like. More specifically, for displacement of the first concave mirror 33 constituting the optical resonator 32, there is employed a resonator length controller which comprises a laminated piezoelectric element composed of PZT or the like and a control device for supplying such an element with a signal proportional to a change of the resonator length (L), and this signal is fed back to thereby form a servo loop. In this structure, the intensity of the light beam emitted from the second harmonics generator 30 can be controlled by controlling the resonator length of the optical resonator 32.

The light beam obtained from the second harmonics generator has a wavelength relative to the second harmonics of the incident beam emitted initially from the laser beam source, but the wavelength of the beam outputted from the second harmonics generator is not limited merely to that of fourth harmonics based on the beam emitted from the solid-state laser medium as described in the embodiments, and may also be that of fifth harmonics as well. In this case, fifth harmonics (wavelength: 213 nm) of a solid-state laser medium composed of Nd:YAG for example can be produced by first synthesizing the beam (wavelength: 1064 nm) emitted from the solid-state laser medium of Nd:YAG and the beam (wavelength: 266 nm) emitted from the second harmonics generator 30, and then transmitting the synthesized beam through another second harmonics generator 30 (using, e.g., urea $CO(NH_2)_2$ of organic crystal as a nonlinear optical crystal element).

Inspection of any dust particle on a reticle can be performed for both faces of the reticle. In this case, the laser beam obtained from the scanning element or the f-θ lens are split into two to scan the two faces of the reticle simultaneously. Although a description has been given above with regard to the dust particle inspection apparatus and method of the present invention relative to a reticle as an article to be inspected, it is to be understood that the article suited for inspection is not limited to a reticle alone. For example, a silicon wafer and any of various compound semiconductor substrates are inspectable as well.

An ordinary reticle consists of a base member composed of a transparent material and a light shield layer patterned on the surface of the base member. Recently, eager researches are in progress to develop a Levenson type phase shift mask and a half-tone type phase shift mask to be employed in place of such a known reticle. The present invention is applicable also for inspecting any of such phase shift masks.

Figure 11A:
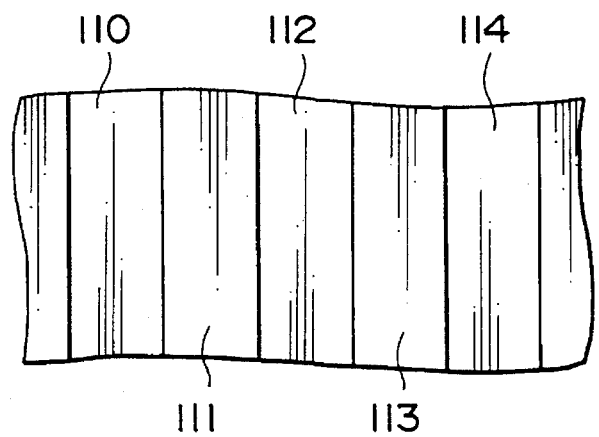
FIGS. 11A to 11C are partially sectional views typically illustrating a phase shift mask and a half-tone type phase shift mask.
Figure 11B:
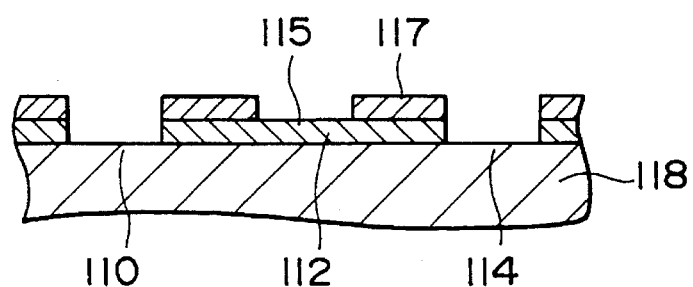
Figure 11C:
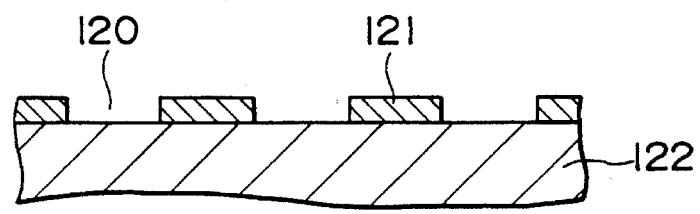

FIG. 11A is a partial plan view typically showing a Levenson type phase shift mask, and FIG. 11B is a partial sectional view typically showing the same mask. In this phase shift mask, the phase of the light beam passed through a beam transmission region A 110 and the phase of the light beam passed through a beam transmission region B 112, where a phase shift layer 115 of SOG for example is formed, are changed by 180° when the phase shift layer 115 has a thickness of $\lambda A/(2(n-1))$. In this expression, A denotes the wavelength of the light beam transmitted through the phase shift mask, and n denotes the refraction index of the material composing the phase shift layer 115. A beam shield layer 117 composed of Cr for example is interposed between the beam transmission region A 110 and the beam transmission region B 112. In a half-tone type phase shift mask shown typically in a partial sectional view of FIG. 11C, the phase of the light beam passed through a beam transmission region 120 And the phase of the light beam passed through a beam semi-shield region 121, which is composed of Cr for example and permits adequate transmission of the light beam therethrough, are changed by 180° if the thickness of the beam semi-shield region 121 is set to a proper value.

Any defect of the phase shift layer in such phase shift mask or any defect of the beam semi-shield region in the half-tone type phase shift mask can be detected completely by the method using the dust particle inspection apparatus of the present invention. Therefore, the term "dust particle" defined in this specification widely connotes any of the above defects as well.

In some cases, the laser beam source in the dust particle inspection apparatus is usable also as an exposure light source for a semiconductor exposer.

According to the present invention, the existence of any dust particle or the like on the surface of an article to be inspected, such as a reticle, is precisely detectable with facility and certainty. It is possible to realize the exact suppression of generation of a speckle pattern. Further in the dust particle inspection apparatus of the present invention, the dimensions of the laser beam source are reducible to be smaller than an A3 size. Consequently the laser beam source can be housed in the casing of the dust particle inspection apparatus to thereby achieve a dimensional reduction of the whole apparatus.

What is claimed is:

1. A dust particle inspection apparatus for detecting any dust particle or the like existent on the surface of an article to be inspected, comprising:

a laser beam source for emitting a laser beam therefrom;

a scanner for scanning the surface of the article, which is to be inspected, with the laser beam emitted from said laser beam source;

an optical detector for detecting the laser beam reflected and diffracted on the surface of said article being inspected;

a stage for setting said article thereon and displacing the same in a predetermined direction; and gas supply means for surrounding said article with a high-purity inert gas atmosphere.

2. The dust particle inspection apparatus according to claim 1, wherein said laser beam source comprises:

an LD-excited solid-state laser capable of emitting second harmonics and consisting of a laser diode, a solid-state laser medium composed of Nd:YAG, and a nonlinear optical crystal element;

a second harmonics generator consisting of a nonlinear optical crystal element and an optical resonator; and a resonator length controller for controlling the resonator length of said optical resonator;

wherein the light beam emitted from said LD-excited solid-state laser is caused to be incident upon said second harmonics generator, and a light beam having the wavelength based on the second harmonics of said incident light beam is emitted from said second harmonics generator.

3. The dust particle inspection apparatus according to claim 2, wherein said laser beam source is equipped with an optical path split means for partially causing the laser beam, which is emitted from said LD-excited solid-state laser, to be incident upon said scanner.

4. The dust particle inspection apparatus according to claim 3, wherein a coherence distance reduction means is disposed between said optical path split means and said scanner.

5. The dust particle inspection apparatus according to claim 2, further including an optical path split means for partially splitting the laser beam emitted from said second harmonics generator; and a coherence distance reduction means disposed between said optical path split means and said scanner.

6. A dust particle inspection method for detecting any dust particle or the like existent on the surface of an article to be inspected, comprising the steps of: surrounding said article with a high-impurity inert gas atmosphere;

while displacing said article in a predetermined direction, scanning the surface of said article with a laser beam having a wavelength $\lambda$ and a coherence distance longer than 1 km; and detecting the laser beam reflected and diffracted on the surface of said article to thereby detect any dust particle or the like on the surface of said article.

7. The dust particle inspection method according to claim 6, further including the step of scanning the region of the said article, where any abnormal light intensity of the reflected and diffracted laser beam has been found on the surface of said article as a result of the foregoing scanning with the laser beam having a wavelength $\lambda$ and a coherence distance longer than 1 km, with another laser beam having a wavelength $\lambda'$ and a coherence distance longer than 1 km.

8. The dust particle inspection method according to claim 7, wherein said two laser beams having the wavelengths $\lambda$ and $\lambda'$ respectively are emitted from the same laser beam source which comprises:

an LD-excited solid-state laser capable of emitting second harmonics and consisting of a laser diode, a solid-state laser medium composed of Nd:YAG, and a nonlinear optical crystal element;

a second harmonics generator consisting of a nonlinear optical crystal element and an optical resonator;

a resonator length controller for controlling the resonator length of said optical resonator; and an optical path split means for partially causing the laser beam, which is emitted from said LD-excited solid-state laser, to be incident upon said scanner;

wherein the laser beam of the wavelength $\lambda$ or $\lambda'$ emitted from said LD-excited solid-state laser is caused to be incident upon said second harmonics generator, and the laser beam of the wavelength $\lambda'$ or $\lambda$ based on the second harmonics of the incident beam is emitted from said second harmonics generator.

9. The dust particle inspection method according to claim 6, further including the step of scanning the region of said article, where any abnormal light intensity of the reflected and diffracted laser beam has been found on the surface of said article as a result of the foregoing scanning with the laser beam having a wavelength $\lambda$ and a coherence distance longer than 1 km, with another laser beam having a coherence distance shorter than 1 km.

* * * * *